United States Patent
Ren

(10) Patent No.: US 12,076,419 B2
(45) Date of Patent: Sep. 3, 2024

(54) LIPIN-1 AS A NOVEL THERAPY TARGET OF MUSCULAR DYSTROPHY

(71) Applicant: Wright State University, Dayton, OH (US)

(72) Inventor: Hongmei Ren, Xenia, OH (US)

( * ) Notice: Subject to any disclaimer, the term of this patent is extended or adjusted under 35 U.S.C. 154(b) by 421 days.

(21) Appl. No.: 16/907,748

(22) Filed: Jun. 22, 2020

(65) Prior Publication Data

US 2020/0397918 A1   Dec. 24, 2020

Related U.S. Application Data

(60) Provisional application No. 62/864,146, filed on Jun. 20, 2019.

(51) Int. Cl.
| | |
|---|---|
| A61K 48/00 | (2006.01) |
| A61K 31/165 | (2006.01) |
| A61K 31/203 | (2006.01) |
| A61K 31/4439 | (2006.01) |
| A61K 35/76 | (2015.01) |
| A61K 35/761 | (2015.01) |
| A61K 35/763 | (2015.01) |
| A61K 38/46 | (2006.01) |
| A61K 47/32 | (2006.01) |
| A61P 21/00 | (2006.01) |

(52) U.S. Cl.
CPC ........ *A61K 48/0058* (2013.01); *A61K 31/165* (2013.01); *A61K 31/203* (2013.01); *A61K 31/4439* (2013.01); *A61K 35/76* (2013.01); *A61K 35/761* (2013.01); *A61K 35/763* (2013.01); *A61P 21/00* (2018.01); *A61K 38/465* (2013.01); *A61K 47/32* (2013.01); *C12N 2750/14143* (2013.01); *C12Y 301/03004* (2013.01)

(58) Field of Classification Search
CPC .. A61K 48/0058; A61K 31/165; A61K 35/76; A61K 35/761
USPC ............................ 424/204.1, 199.1; 514/44 R
See application file for complete search history.

(56) References Cited

U.S. PATENT DOCUMENTS

| | | | |
|---|---|---|---|
| 10,286,085 B2 * | 5/2019 | Passananti | ......... G01N 33/6893 |
| 2016/0279255 A1 * | 9/2016 | Wilson | ................. C12N 9/1205 |
| 2019/0048337 A1 * | 2/2019 | Hsu | ....................... C12N 15/907 |

OTHER PUBLICATIONS

Meijer et al., "LPIN1 deficiency with severe recurrent rhabdomyolysis and persistent elevation of creatine kinase levels due to chromosome 2 maternal isodisomy". Molecular Genetics and Metabolism Reports. Nov. 8, 2015.5. 85-88. (Year: 2015).*
Higashida et al., "Potential role of lipin-1 in exercise-induced mitochondrial biogenesis". Biochemical and Biophysical Research Communications. Jul. 24, 2008. 374(3):587-591 (Year: 2008).*
Luten et al., "Biodegradable polymers as non-viral carriers for plasmid DNA delivery" Journal of Controlled Release. Mar. 3, 2008.126(2):97-110 (Year: 2008).*
Krueger et al., "Identification of Retinoic Acid in a High Content Screen for Agents that Overcome the Anti-Myogenic Effect of TGF-Beta-1". PLoS ONE, Nov. 30, 2010. 5(11): 1-11 (Year: 2010).*
Kabanov et al., "Pluronic block copolymers: novel functional molecules for gene therapy". Adv Drug Deliv Rev. Feb. 21, 2002. 54(2): 223-233 (Year: 2002).*
Nowak et al., "Duchenne muscular dystrophy and dystrophin: pathogenesis and opportunities for treatment". EMBO Rep. Sep. 2004; 5(9):872-6 (Year: 2004).*
Rashid et al., "Lipin1 deficiency causes sarcoplasmic reticulum stress and chaperone-responsive myopathy". EMBO J. Jan. 3, 2019; 38(1):pp. 1-21. (Year: 2019).*
Elangkovan et al., "Gene Therapy for Duchenne Muscular Dystrophy". J Neuromuscul Dis. 2021;8(s2):S303-S316 (Year: 2021).*

* cited by examiner

*Primary Examiner* — Anne Marie S Wehbe
*Assistant Examiner* — Hanan Isam Abuzeineh
(74) *Attorney, Agent, or Firm* — Dinsmore & Shohl LLP

(57) ABSTRACT

Methods for treatment of Duchenne's muscular dystrophy and several clinically related conditions in subjects in need thereof are provided. In further aspects, methods are provided for decreasing muscle degeneration in a subject in need thereof. In even further aspects, methods of enhancing sarcolemma stability and or/integrity in muscle cells lacking functional dystrophin in a subject in need thereof are provided. In aspects, the above-methods comprise administering a therapeutically effective amount of a composition suitable for increasing expression of a LPIN1 gene or a lipin-1 protein levels in a muscle cell of said subject; and decreasing muscle degeneration and improving exercise endurance and muscle contractile force in said subject by said step of administering.

23 Claims, 8 Drawing Sheets

LIPIN-1 AS A NOVEL THERAPY TARGET OF MUSCULAR DYSTROPHY

RELATED APPLICATIONS

This application claims priority to US Provisional Patent Application 62/864,146, filed Jun. 20, 2019, the contents of which are hereby incorporated by reference in its entirety.

TECHNICAL FIELD

Embodiments described herein relate generally to treatment of subjects with dystrophic muscle disorders.

BACKGROUND

Duchenne's muscular dystrophy (hereinafter "DMD") is caused by loss of dystrophin, which plays an important role in muscle structure. Loss of dystrophin causes instability of the sarcolemma (the muscle cell membrane), leading to membrane damage during muscle contraction. This damage causes repeated cycles of cellular death and slow or debilitated regeneration of muscle fibers in affected boys. Eventually, the muscle's regenerative capacity becomes exhausted, muscle is no longer capable of being replaced and is irreparably weakened, which ultimately leads pulmonary failure through the loss of the ability to adequately contract the lungs and effectively breathe and, consequently, the patient's untimely death.

The primary goal in treating DMD is to reverse or at least prevent the instability of the sarcolemma in order to prevent the repeated cycles of degeneration and regeneration that leads to weakness, paralysis, and death. Previous approaches have tried to reverse the instability of the sarcolemma by increasing dystrophin levels, with some groups attempting to deliver a functional dystrophin protein to the cell using gene therapy methods. These attempts have met difficulties in achieving improved sarcolemma stability due to several hurdles. For example, gene therapy treatments of DMD have not been successful because the dystrophin protein is so large that the dystrophin gene cannot be packaged into current gene therapy vectors. While exon skipping strategies have been proposed for DMD treatment, they have limited applicability.

SUMMARY

Based on the foregoing, a treatment for increasing the stability of the sarcolemma in subjects with DMD, as well as related disorders such as rhabdomyolysis, age-related muscle loss, and other types of muscular dystrophy sharing common features associated with decreased lipin-1 expression, is highly sought after. Various embodiments of the instantly-disclosed methods described herein meet those needs by making the sarcolemma more elastic so that it can withstand the structural stress occurring in the absence of dystrophin, thereby preventing excessive damage to the sarcolemma and improving its stability. More specifically, by increasing muscle cells' expression of the protein lipin-1 through the instantly-disclosed methods, the sarcolemma is stabilized, resulting in reduced muscle fiber degeneration, increased muscle mass, and improved muscle strength.

Lipin-1 is a phosphatidic acid phosphatase that regulates the biosynthesis of the membrane lipid diacylglycerol (hereinafter "DAG"). DAG is the precursor of several glycerophospholipids, which are the main constituents of cell membranes, including phosphatidylcholine, ethanolamine, and serine. DAG is also a signaling molecule that regulates mitochondrial function and MEF2C expression during the formation of muscle tissue. Dysfunctional lipin-1 signaling causes defects in sarcolemma fluidity that contributes to membrane breakdown in DMD.

This disclosure herein relates generally to methods of treating a dystrophic muscle disorder or general muscle weakness and wasting in a subject in need thereof. The methods disclosed herein increase lipin-1 protein levels in a subject's cells, thereby increasing lipin-1 protein activity. In aspects, the methods feature administering a therapeutically effective amount of a composition suitable for increasing expression of a LPIN1 gene or a lipin-1 protein in a muscle cell of said subject. The increases can be beneficial to increases muscle mass, muscle strength, and/or exercise endurance in the subject. In some aspects, the methods are applied to subjects with a dystrophic muscle disorder such as DMD, rhabdomyolysis, age-related muscle loss or a muscular dystrophy sharing common features of decreased lipin-1 expression.

According to one aspect of the present disclosure, methods of treating a dystrophic muscle disorder in a subject in need thereof are provided. In some aspects, the method comprises administering a therapeutically effective amount of a composition suitable for increasing expression of a LPIN1 gene or a lipin-1 protein levels in a muscle cell of said subject; and increasing expression of a LPIN1 gene or a lipin-1 protein in said subject by said step of administering. In some aspects, the composition comprises the LPIN1 gene, which in may be introduced into a subject's muscle cells through approaches such as gene therapy. In other aspects, the LPIN1 gene is introduced into a subject's muscle cells through a viral vector. In certain aspects, the composition comprises an agonist of a LPIN1 gene activation or a lipin-1 protein expression. In further aspects, the dystrophic muscle disorder is DMD or rhabdomyolysis or age-related muscle loss. In other aspects, the dystrophic muscle disorder is a muscular dystrophy sharing common features of decreased lipin-1 expression.

In some aspects, methods of decreasing muscle degeneration in a subject in need thereof are provided. In certain aspects, the method comprises administering a therapeutically effective amount of a composition suitable for increasing activation of a LPIN1 gene or expression of a lipin-1 protein to increase levels in a muscle cell of said subject; and decreasing muscle degeneration in said subject by said step of administering. In some aspects, the composition comprises the LPIN1 gene, which may be introduced into a subject's muscle cells, such as through gene therapy. In some instances, the LPIN1 gene is introduced into a subject's muscle cells through a viral vector. In other instances, the composition features an agonist of a LPIN1 gene activation/transcription or expression/translation of a lipin-1 protein. In some aspects, the subject suffers from a dystrophic muscle disorder, such as DMD, rhabdomyolysis or age-related muscle loss. In certain aspects, the dystrophic muscle disorder is a muscular dystrophy disorder or condition sharing common features of decreased LPIN1 gene activity and/or a lipin-1 protein expression.

In some aspects, methods for enhancing sarcolemma stability and or/integrity in muscle cells lacking functional dystrophin are provided. In certain aspects, the method comprises administering a therapeutically effective amount of a composition suitable for increasing expression of a LPIN1 gene or a lipin-1 protein levels in a muscle cell of said subject; and enhancing sarcolemma stability and/or integrity in said subject by said step of administering. In certain aspects, the composition features the LPIN1 gene, which in some aspects may be introduced into a subject's muscle cells through gene therapy. In further aspects, the LPIN1 gene may be introduced into a subject's muscle cells through a viral vector. In other aspects, the composition features an agonist of a LPIN1 gene activation or of lipin-1 protein expression. The subject may suffer from a dystrophic muscle disorder, such as DMD or rhabdomyolysis or age-related muscle loss. In further aspects, the dystrophic muscle disorder is a muscular dystrophy sharing common features of decreased lipin-1 protein expression through decreased expression of LPIN1. In some aspects, administering a therapeutically effective amount of a composition suitable for increasing expression of a LPIN1 gene or lipin-1 protein levels in a muscle cell of said subject reduces muscle fiber degeneration. In some aspects, administering a therapeutically effective amount of a composition suitable for increasing expression of a LPIN1 gene or lipin-1 protein levels in a muscle cell of said subject increases muscle mass, increases muscle strength, and/or increases exercise endurance. In some aspects administering a therapeutically effective amount of a composition suitable for increasing expression of a LPIN1 gene or lipin-1 protein levels in a muscle cell of said subject decreases centrally nucleated muscle fibers. According to another aspects, increased expression of lipin-1 protein is used as a treatment for subjects with DMD, as well as related disorders such as rhabdomyolysis, age-related muscle loss, and other types of muscular dystrophy sharing common features associated with decreased lipin-1 expression.

In some aspects of the instantly-disclosed methods, the composition is a LPIN1 gene or a nucleotide sequence or a polynucleotide encoding lipin-1. The LPIN1 gene or the lipin-1 protein may be derived from the human sequences of such. The nucleotide may be further operably placed in a vector, such as a viral vector or a plasmid. A viral vector may be derived from an adeno-associated virus ("AAV"), a retrovirus, a lentivirus, an adenovirus, a herpes simplex virus, a cytomegalovirus, a poxvirus, a Simian virus 40 (SV40) an Epstein-Barr virus or combinations thereof. Vectors may further feature a promoter, such as an a skeletal muscle actin promoter, a myosin light chain 3F promoter, or a muscle creatine kinase promoter. Vectors may further include a muscle-specific enhancer, such as an SV40 enhancer.

In some aspects of the instantly-disclosed methods, the composition features a plasmid delivery system containing a LPIN2 gene or a polynucleotide encoding lipin-1 or a lipin-1 protein. The plasmid delivery system may further feature a lipid, a liposome, a polymer, a lipoplex, a peptide, and/or a protein. The lipid in the plasmid delivery system may be cationic. The polymer in the plasmid delivery system may be non-ionic, such as. poly N-vinyl pyrrolidone. The peptide or protein may be one or more of a poly-L-lysine, a viral fusion peptide, a transferrin, a GALA peptide, and a KALA peptide. The plasmid delivery system may feature a mix of block co-polymers and pluronics L61 and F127, such as SP1017. The plasmid delivery system may utilize CRISPR and Cas-9 to deliver the LPIN1 gene or lipin-1 protein.

In some aspects, the methods may also feature co-administration transcriptional activator, such as retinoic acid and/or trichostatin.

In further aspects of the present disclosure, including the instantly-disclosed methods, the administered composition is rosiglitazone. In other aspects, the composition is one or more of the following agents: a peroxisome proliferator-activated receptor γ coactivator 1 α (PGC-1α) agonist, a sterol regulatory element binding protein (SREBP) agonist, nuclear factor Y, dexamethasone, formoterol, a NOR-1 agonist or combinations thereof.

These and other embodiments are described in more detail in the following Detailed Description, as well as the appended drawings. The accompanying drawings are included to provide a further understanding of the various embodiments, and are incorporated into and constitute a part of this specification. The drawings illustrate the various embodiments described herein, and together with the description, serve to explain the principles and operations of the claimed subject matter.

BRIEF DESCRIPTION OF THE DRAWINGS

Referring now to the illustrative examples in the drawings:

FIG. 1A is a representative immunofluorescence staining of gastrocnemius muscle cross-sections from mdx mice two weeks after administration of AAV1-lipin1. Lipin-1 expression was restored by intramuscular injection of 5×10' viral genome particles (vg)/mouse AAV1-lipin1 into the gastrocnemius muscle of mdx mice. FIG. 1A shows cryostat cross-section stained with anti-HA antibody to detect transfected lipin-1 (red). Arrows in the right panels indicate centrally nucleated myofibers characteristic of cumulative muscle regeneration. Scale bar=250 μm. FIG. 1B is a graph showing quantification of the percentage of centrally nucleated myofiber in total myofibers in the lipin-1 restored regions compared with the non-restored regions. FIG. 1C is a graph depicted the size distribution of muscle fiber cross-sectional area (CSA) in the lipin-1 restored regions or non-restored regions. Ten randomly selected cross-sections from each muscle were used (n=5 mice for each group).

FIG. 2A is a co-immunofluorescence analysis of lipin-1 (red) and embryonic myosin heavy chain ("eMHC", green). Immunostaining with eMHC was used to assess the effects of lipin-1 restoration on current myofiber regeneration in dystrophic muscle. FIG. 2A shows muscle tissue sections from AAV1-lipin1-treated mdx mice or saline-injected mdx mice as controls. Scale bar=100 μm. FIG. 2B is a graph showing quantification of the percentage of eMHC-positive fibers (n=6 mice for each group). The error bar indicates the mean with S.D. $p<0.05$.

FIG. 3A shows immunofluorescent images of IgG staining in gastrocnemius muscle sections from AAV1-lipin1-treated mdx mice and saline-injected mdx mice. Scale bar=250 μm. FIG. 3B is a graph showing quantification of IgG-positive fibers as a percentage of total fibers counted in each section (*$p<0.05$; n=5 mice for each group).

FIG. 4A is a Western blot showing restoration of lipin-1 protein levels. Lipin-1 was restored by intramuscular injection of lipin-1 virus in gastrocnemius of mdx male mice at 2 months old. Mdx male littermates injected with saline and B10 mice served as controls. One month after injection, the gastrocnemius muscles were harvested for Western blotting to detect the levels of lipin-1 expression in these groups of mice. FIG. 4A shows this Western blot. FIG. 4B is a graph showing quantification of the band intensity of the bands in the Western blot. FIG. 4C is a graph showing the time to exhaustion running on a treadmill of B10-WT, mdx-saline, and mdx-lipin1 mice. (n=5-9 male mice per group, 2-3 months old; **$p<0.01$; *$p<0.05$).

FIG. 5A shows in situ force-frequency curves of gastrocnemius muscles from lipin-1 restored mdx mice which showed significant force improvement compared to saline treated mice. FIG. 5B is a graph showing that lipin-1 restoration regained specific force of gastrocnemius muscles in mdx mice at 100 Hz (n=5-6 mice per group; mdx-saline vs. mdx-lipin1, *$p<0.05$, **$p<0.01$).

FIG. 6A shows a Western blot of lipin1 expression in B10 WT, mdx$^{Stop-lipin1}$ controls and transgenic mdx$^{lipin1-KI}$ mice. FIG. 6B shows representative immunofluorescence images of EBD staining in gastrocnemius sections from these mice. Muscle sections were immunostained with laminin (green) and counter-stained with DAPI (blue) (scale bar=100 μm); FIG. 6C shows quantitation of EBD positive fibers; and, FIG. 6D shows centrally nucleated myofibers as a percentage of total fibers in composited images (*$p<0.05$; n=6 mice/group).

FIG. 7A shows a Western blot of lipin1 expression in B10 WT, mdx controls and mdx$^{liPin1-/-}$ mice. FIG. 7B shows representative immunofluorescence images of IgG staining in gastrocnemius sections from mdx and mdx$^{lipin1-/-}$ mice. Scale bar=100 μm.

DETAILED DESCRIPTION

Figure 1A:
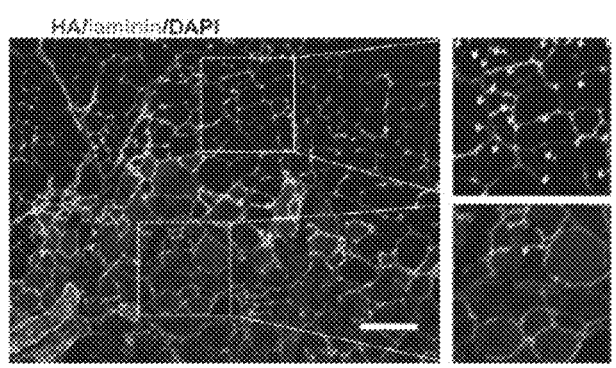
FIG. 1A-C demonstrate that restoring lipin-1 levels significantly reduced central nucleation and fiber size variability in muscle fibers of $DMD^{mdx}$ mice (hereinafter "mdx mice").

Specific aspects of the present application will now be described. The disclosure may, however, be exemplified or practiced in different forms and should not be construed as limited to the descriptions set forth in this disclosure. Rather, these descriptions are provided to convey the scope of the subject matter to those skilled in the art such that they can comprehend and appreciate the full scope and potential of the disclosure. Additionally, any examples set forth in this specification are not presented as demonstrations of any limitations and merely set forth some of the any possible aspects of the invention.

All scientific and technical terms used herein have meaning commonly used in the art unless otherwise specified. Such terms are found defined and used in context in various standard references illustratively including M. R. Green and J. Sambrook, Molecular Cloning: A Laboratory Manual, Cold Spring Harbor Laboratory Press; 4th Ed., 2012; F. M. Ausubel, Ed., Short Protocols in Molecular Biology, Current Protocols; 5th Ed., 2002; B. Alberts et al., Molecular Biology of the Cell, 4th Ed., Garland, 2002; CRISPR/Cas: A Laboratory Manual, Doudna and *Mali* (eds), Cold Spring Harbor Laboratory Press, Cold Spring Harbor, NY, USA, 2016; D. L. Nelson and M. M. Cox, Lehninger Principles of Biochemistry, 4th Ed., W.H. Freeman & Company, 2004; Herdewijn, P. (Ed.), Oligonucleotide Synthesis: Methods and Applications, Methods in Molecular Biology, Humana Press, 2004; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, PA: Lippincott, Williams & Wilkins, 2004; and L. Brunton et al., Goodman & Gilman's The Pharmacological Basis of Therapeutics, McGraw-Hill Professional, 12th Ed., 2011. The definitions provided herein are to facilitate understanding of certain terms used frequently herein and are not meant to limit the scope of the present disclosure.

The presently-disclosed data demonstrate that lipin-1 protein levels are dramatically reduced in the muscle of DMD subjects and in a DMD mouse model. Surprisingly, the studies presented herein identified that administration of a therapeutically effective amount of a composition suitable for increasing expression of a LPIN1 gene or a lipin-1 protein levels in a muscle cell of a subject suffering from DMD greatly reduced muscle fiber degeneration, improved muscle mass, and led to impressive gains in strength. Thus, the presently-disclosed data demonstrate a new concept of methods for treating a dystrophic muscle disorder in a subject in need thereof, including administering a therapeutically effective amount of a composition suitable for increasing expression of a LPIN1 gene or a lipin-1 protein levels in a muscle cell of said subject.

Accordingly, in some aspects, the presently-disclosed subject matter includes methods of treating a dystrophic muscle disorder in a subject in need thereof. In some aspects, the methods include administering a therapeutically effective amount of a composition suitable for increasing expression of a LPIN1 gene or a lipin-1 protein levels in a muscle cell of said subject; and increasing expression of a LPIN1 gene or a lipin-1 protein in said subject by said step of administering.

As used herein, the term "treating" relates to any treatment of a dystrophic muscle disorder, including but not limited to prophylactic treatment and therapeutic treatment. A "dystrophic muscle disorder" includes any form of skeletal, cardiac and smooth muscle weakness and wasting (e.g. muscular dystrophy, cardiomyopathy, respiratory muscle weakness and the like). "Treating" may include any effect, e.g., lessening, reducing, modulating, or eliminating, that results in the improvement of a dystrophic muscle disorder. Similarly, "treating" may also include increasing or stimulating certain responses, such as LPIN1 or lipin-1 expression, that assist in or lead to improvement of a dystrophic muscle disorder. "Treating" or "treatment" of a dystrophic muscle disorder may include: inhibiting a dystrophic muscle disorder, i.e., arresting the development of the dystrophic muscle disorder or its clinical symptoms; or relieving the dystrophic muscle disorder, i.e., causing temporary or permanent regression of the dystrophic muscle disorder or its clinical symptoms.

A "subject" may include mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like).

An "effective amount" or "therapeutically effective amount" as defined herein in relation to the treatment of a dystrophic muscle disorder may refer to an amount of the composition suitable for increasing expression of a LPIN1 gene or a lipin-1 protein levels in a muscle cell of said subject that can decrease, reduce, or inhibit, or otherwise abrogate the dystrophic muscle disorder. An "effective amount" as used herein also may include an amount sufficient to delay the development of a symptom of a dystrophic muscle disorder, alter the course of a dystrophic muscle disorder (for example but not limited to, slow the progression of a symptom of the dystrophic muscle disorder), or reverse a symptom of the dystrophic muscle disorder. An "effective amount" may vary depending on the administered composition suitable for increasing expression of a LPIN1 gene or a lipin-1 protein levels in a muscle cell of said subject, the specific dystrophic muscle disorder and its severity, as well as the age, weight, etc., of the subject to be treated. Additionally, the dosage can vary depending upon the dosage form employed and the route of administration utilized.

In some aspects of a method of treating a dystrophic muscle disorder in a subject in need thereof, the method features providing or administering a composition comprising a LPIN1 gene to a subject or to a cell. In aspects, the LPIN1 gene is introduced into a subject's muscle cells using gene therapy or by providing a polynucleotide encoding a lipin-1 protein by transduction or transfection. In aspects, the LPIN1 gene expression is controlled or influenced by a muscle specific promoter, typically placed upstream in the 5' direction of the LPIN1 gene, such as an a skeletal muscle actin promoter, a myosin light chain 3F promoter, or a muscle creatine kinase promoter. In some aspects, the LPIN1 gene provided further features a muscle-specific enhancer to improve expression or site-specific expression, such as an SV-40 enhancer. In other aspects, the LPIN1 gene therapy regimen further features co-administration, either simultaneously or sequentially, of one or more transcriptionally active drugs, such as retinoic acid or trichostatin A, so as to further stimulate the expression of lipin-1.

By way of example, a LPIN1 gene in *Homo sapiens* is assigned to Gene ID 23175 and may be found on chromosome 2p25.1, with a cDNA accession no. of NM_145693 and a protein ID of C114693. A murine homolog has an MGI ID of 1891340 and a gene id of 14245.

Those skilled in the art will appreciate that in some instances, administration of a DNA encoding a lipin-1 protein (e.g. cDNA) without exons present in the gene may be preferred, particularly in instances where an administered LPIN1 will not undergo or be able to undergo splicing. It should be recognized that as used herein, reference to a "gene" includes both a native chromosomal sequence, as well as nucleotide sequences of assembled introns (i.e. exon spliced) or a cDNA of a full-length lipin-1 protein. It should also be recognized that as used herein, reference to LPIN1 genes and/or lipin-1 protein includes all variants, chimeras, fusions or truncations that retain functional protein activity.

It should also be recognized that reference to a LPIN1 gene or a lipin-1 protein may include additional nucleotides (or corresponding peptides) to append additional functionality to a lipin-1 protein. For example, a tag may be fused to a lipin-1 protein. Tags may be fused at or near a terminus of lipin-1. Such tags may further include a cleavage sequence so a tag may be removed if desired, such as Factor Xa, thrombin, SUMOstar protein, TEV protease, or trypsin. A tag may include a purification tag, such as a 6× His tag, FLAG, biotin, ubiquitin, SUMO, streptavidin or other tags known in the art. Other tags and purification systems are similarly operable. Techniques for the expression and purification of recombinant proteins are known (see, e.g., Green and Sambrook Eds., Molecular Cloning: A Laboratory Manual 4th ed. (Cold Spring Harbor, N.Y. 2012).

Further fusion options also include a detection label such as a radiolabel or a fluorescent detection label such as a fluorescent protein, or similar at or proximal to the N-terminus, C-terminus or both. A fluorescent protein fusion optionally emits in the green, red, or blue regions of the visible spectrum.

A gene encoding a lipin-1 protein may be inserted or ligated into a suitable vector for expression in a cell. Standard techniques are available to construct suitable vectors containing the appropriate nucleic acids and transcriptional/translational control sequences in order to operably achieve protein or peptide expression in a variety of host-expression systems. Specific initiation signals and translational control signals may also be required for efficient translation of the LPIN1 gene. Such signals include an ATG initiation codon and adjacent sequences. One may also incorporate into the transcriptional unit an appropriate polyadenylation (poly (A)) site if one was not contained within the original segment.

In some instances, the LPIN1 gene is introduced into a subject's muscle cells through a viral vector, such as an adeno-associated virus ("AAV"), a retrovirus, a lentivirus, an adenovirus, a herpes simplex virus, a cytomegalovirus, a poxvirus, a Simian virus 40 (SV40) or an Epstein-Barr virus. Those skilled in the art will appreciate that any viral vector may feature further additions, substitutions or mutations to the nucleotide sequences therein to render such fit for safe application.

In other aspects of a method of treating a dystrophic muscle disorder in a subject in need thereof, the gene therapy involves non-viral gene delivery of the LPIN1 gene. In such approaches, the gene therapy employs a plasmid as the vector of the LPIN1 gene. The plasmid may be introduced into the muscle cells using a plasmid delivery system including of one or more of the following: lipids, liposomes, polymers, lipoplexes, peptides, and proteins. In some instances, the lipids in the plasmid delivery system may be cationic. In some instances, the polymers in the plasmid delivery system are non-ionic, such as poly N-vinyl pyrrolidone. The plasmid delivery system may employ an amphiphilic carrier, such as SP1017, which is a mix of block co-polymers and pluronics L61 and F127. The peptides or proteins in the plasmid delivery system may include one or more of the following: poly-L-lysine, viral fusion peptides, transferrin, GALA peptide, and KALA peptide. In some instances, the delivery of the plasmid into muscle cells may be enhanced by one or more of the following mechanisms: electroporation, ultrasound, and microbubbles. In aspects, the gene therapy employs the CRISPR/Cas-9 system to deliver the LPIN1 gene to the muscle cells.

In some aspects, the methods disclosed herein feature administering or providing a lipin-1 protein to a cell, such as a recombinant or isolated lipin-1 protein. Proteins may be provided as a form of protein therapy, such as with nanocarriers, CPP (cell penetrating peptide) fusion, co-administration of destabilizing agents or chemicals, such as saporin, penetratin, poly-histidine, chloroquine, methylamine, and polyethylenimine.

In further aspects of a method of treating a dystrophic muscle disorder in a subject in need thereof, the composition features an agonist of a LPIN1 gene or a lipin-1 protein. In such aspects, the agonist may be a peroxisome proliferator-activated receptor γ coactivator 1α (PGC-1α) agonist. In other aspects, the agonist may be a sterol regulatory element binding protein (SREBP) agonist. In further aspects, a LPIN1 gene or a lipin-1 protein expression may be stimulated by nuclear factor Y. The agonist may further be a glucocorticoid receptor agonist, such as dexamethasone, or a $\beta_2$-adrenoreceptor agonist, such as formoterol. In some instances, the agonist may be a NOR-1 agonist.

In further instances of the present disclosure, the methods for treating a dystrophic muscle disorder feature administering a thiazolidinedione compound (or glitazone) or homolog thereof to a subject in need. Thiazolidinedione compounds include rosiglitazone and piolitazone. As set forth in the examples herein, it has been identified that administration of a thiazolidinedione, such as rosiglitazone, may stimulate or upregulate, or even preserve (e.g. reduce degradation), the expression of lipin-1 in a cell. As identified herein, administration of a thiazolidinedione increases the quantity of lipin-1 protein within a cell. Such increase may be through increased transcription or decreased degradation or combinations thereof. As further illustrated herein, increased lipin-1 protein expression allows for an improved response in a dystrophic muscle disorder.

Administration of a thiazolidinedione, such as rosiglitazone or pioglitazone, may be through known techniques in the art. For example, thiazolidinediones have good bioavailability and absorption following oral administration. Other routes may be utilized as well, particularly if certain administrative effects are desired, such as site specific delivery, avoidance of first-pass, rapid systemic delivery, delayed or prolonged delivery and the like. Other routes of administration may include intramuscular, intravenous, sublingual, intraperitoneal, inhalation, transdermal, electroporation, gene gun or subcutaneous administration or combinations thereof.

In some aspects of the present disclosure, the dystrophic muscle disorder is DMD. In other aspects, the dystrophic muscle disorder is rhabdomyolysis or age-related muscle loss. In further aspects, the dystrophic muscle disorder is a muscular dystrophy sharing common features of decreased lipin-1 expression.

In some aspects, methods of decreasing muscle degeneration in a subject in need thereof are provided. In such aspects, the method comprises administering a therapeutically effective amount of a composition suitable for increasing expression of a LPIN1 gene or a lipin-1 protein levels in a muscle cell of said subject; and decreasing muscle degeneration in said subject by said step of administering.

With regard to aspects of a method of decreasing muscle degeneration in a subject in need thereof, the composition may feature a LPIN1 gene or a polynucleotide encoding a lipin-1 protein. In some instances, the LPIN1 gene may introduced into a subject's muscle cells using a gene therapy or similar for providing to a cell of the subject a nucleic acid sequence or polynucleotide encoding a lipin-1 protein. In some aspects, the nucleotides of the LPIN1 gene may be operably paired or linked with a muscle specific promoter, such as an a skeletal muscle actin promoter, a myosin light chain 3F promoter, or a muscle creatine kinase promoter. In further aspects, the LPIN1 gene may be paired with a muscle-specific enhancer, such as an SV-40 enhancer. In further aspects, LPIN1 gene therapy may further feature co-administration with one or more transcriptionally active drugs, such as retinoic acid or trichostatin A, so as to further stimulate the expression of lipin-1. In certain aspects, the LPIN1 gene may be introduced into a subject's muscle cells through a viral vector. In other aspects, the LPIN1 gene may be introduced into muscle cells of the subject using one of the following viral vectors: adeno-associated virus, retrovirus, lentivirus, adenovirus, pox virus, herpes simplex virus, or Epstein-Barr virus.

In further aspects of a method of decreasing muscle degeneration in a subject in need thereof, gene therapy may involve non-viral gene delivery of the LPIN1 gene. In such aspects, the gene therapy may employ a plasmid as a vector for the LPIN1 gene. The plasmid may be introduced into the subject's muscle cells using a plasmid delivery system that may feature one or more of the following: lipids, liposomes, polymers, lipoplexes, peptides, and proteins. In some aspects, the lipids in the plasmid delivery system are cationic. In further aspects, the polymers in the plasmid delivery system may be non-ionic, such as poly N-vinyl pyrrolidone. The plasmid delivery system may employ an amphiphilic carrier, such as SP1017, which is a mix of block co-polymers and pluronics L61 and F127. Peptides or proteins in a plasmid delivery system may also include one or more of the following: poly-L-lysine, viral fusion peptides, transferrin, GALA peptide, and KALA peptide. In some instances, delivery of the plasmid into muscle cells may be enhanced by one or more of the following mechanisms: electroporation, ultrasound, and microbubbles. In further aspects, the gene therapy may utilize a CRISPR/Cas-9 system to deliver the LPIN1 gene to the muscle cells.

With further regard to methods to decrease muscle degeneration in a subject in need thereof, the composition may feature an agonist of a LPIN1 gene or a lipin-1 protein. In some aspects, the agonist may be a peroxisome proliferator-activated receptor γ coactivator 1 α (PGC-1α) agonist or a sterol regulatory element binding protein (SREBP) agonist. In certain aspects, LPIN1 gene or a lipin-1 protein expression may be stimulated by nuclear factor Y. In further aspects, the agonist may be a glucocorticoid receptor agonist, such as dexamethasone, or a $\beta_2$-adrenoreceptor agonist, such as formoterol. In other aspects, the agonist may be a NOR-1 agonist.

In further aspects, the methods for decreasing muscle degeneration in a subject in need thereof feature administering a thiazolidinedione compound (or glitazone) or homolog thereof to a subject in need. Thiazolidinedione compounds include rosiglitazone and piolitazone. Administration of a thiazolidinedione, such as rosiglitazone or pioglitazone, may be through known techniques in the art. For example, thiazolidinediones have good bioavailability and absorption following oral administration. Other routes may be utilized as well, particularly if certain administrative effects are desired, such as site specific delivery, avoidance of first-pass, rapid systemic delivery, delayed or prolonged delivery and the like. Other routes of administration may include intramuscular, intravenous, sublingual, intraperitoneal, inhalation, transdermal, electroporation, gene gun or subcutaneous administration or combinations thereof.

In aspects of a method of decreasing muscle degeneration in a subject in need thereof, the subject suffers from a dystrophic muscle disorder. In some instances, the dystrophic muscle disorder is DMD. In other instances, the dystrophic muscle disorder is rhabdomyolysis or age-related muscle loss. In even further instances, the dystrophic muscle disorder is a muscular dystrophy sharing common features of decreased LPIN1 gene or a lipin-1 protein expression.

In some aspects, the disclosure herein provides methods of enhancing sarcolemma stability and or/integrity in muscle cells lacking functional dystrophin in a subject in need thereof are provided. In such aspects, the method comprises administering a therapeutically effective amount of a composition suitable for increasing expression of a LPIN1 gene or a lipin-1 protein levels in a muscle cell of said subject; and enhancing sarcolemma stability and/or integrity in said subject by said step of administering.

In aspects of a method of enhancing sarcolemma stability and or/integrity in muscle cells lacking functional dystrophin in a subject in need thereof, the composition may feature a LPIN1 gene. A LPIN1 gene may be introduced into a subject's muscle cells using gene therapy. In some regards, the LPIN1 gene may be operably paired with a muscle specific promoter, such as an a skeletal muscle actin promoter, a myosin light chain 3F promoter, or a muscle creatine kinase promoter. In other aspects, the LPIN1 gene may be paired or further paired with a muscle-specific enhancer, such as an SV-40 enhancer. The LPIN1 gene therapy may further feature co-administration with one or more transcriptionally active drugs, such as retinoic acid or trichostatin A, so as to further stimulate the expression of lipin-1. In some instances, the LPIN1 gene may be introduced into a subject's muscle cells through a viral vector, such as: adeno-associated virus, retrovirus, lentivirus, poxvirus, adenovirus, herpes simplex virus, or Epstein-Barr virus.

In aspects of a method of enhancing sarcolemma stability and or/integrity in muscle cells lacking functional dystrophin in a subject in need thereof, the gene therapy may also or alternatively feature non-viral gene delivery of the LPIN1 gene. In such regards, the gene therapy may employ a plasmid as the vector of the LPIN1 gene. The plasmid may be introduced into the subject's muscle cells using a plasmid delivery system featuring one or more of the following: lipids, liposomes, polymers, lipoplexes, peptides, and proteins. The lipids in the plasmid delivery system may be cationic and the polymers in the plasmid delivery system may be non-ionic, such as poly N-vinyl pyrrolidone. The plasmid delivery system may employ an amphiphilic carrier, such as SP1017, which is a mix of block co-polymers and pluronics L61 and F127. The peptides or proteins in the plasmid delivery system may include one or more of the following: poly-L-lysine, viral fusion peptides, transferrin, GALA peptide, and KALA peptide. In some instances, the delivery of the plasmid into muscle cells may be enhanced by one or more of the following mechanisms: electroporation, ultrasound, and microbubbles. The gene therapy may also employ the CRISPR/Cas-9 system to deliver the LPIN1 gene to the muscle cells.

In aspects of a method of enhancing sarcolemma stability and or/integrity in muscle cells lacking functional dystrophin in a subject in need thereof, the composition may feature an agonist of a LPIN1 gene or a lipin-1 protein, such as a peroxisome proliferator-activated receptor γ coactivator 1 α (PGC-1α) agonist and/or a sterol regulatory element binding protein (SREBP) agonist. In other aspects, LPIN1 gene or a lipin-1 protein expression is stimulated by nuclear factor Y. In further aspects, the agonist is a glucocorticoid receptor agonist, such as dexamethasone and/or a $β_2$-adrenoreceptor agonist, such as formoterol. In further aspects, the agonist is a NOR-1 agonist.

In further aspects, the methods for enhancing sarcolemma stability and or/integrity in muscle cells lacking functional dystrophin in a subject in need thereof feature administering a thiazolidinedione compound (or glitazone) or homolog thereof to a subject in need. Thiazolidinedione compounds include rosiglitazone and piolitazone. Administration of a thiazolidinedione, such as rosiglitazone or pioglitazone, may be through known techniques in the art. For example, thiazolidinediones have good bioavailability and absorption following oral administration. Other routes may be utilized as well, particularly if certain administrative effects are desired, such as site specific delivery, avoidance of first-pass, rapid systemic delivery, delayed or prolonged delivery and the like. Other routes of administration may include intramuscular, intravenous, sublingual, intraperitoneal, inhalation, transdermal, electroporation, gene gun or subcutaneous administration or combinations thereof.

In aspects of a method of enhancing sarcolemma stability and or/integrity in muscle cells lacking functional dystrophin in a subject in need thereof, the subject suffers from a dystrophic muscle disorder, such as DMD. In other aspects, the dystrophic muscle disorder is rhabdomyolysis or age-related muscle loss. In further aspects, the dystrophic muscle disorder is a muscular dystrophy sharing common features of decreased LPIN1 gene or a lipin-1 protein expression.

In aspects of a method of enhancing sarcolemma stability and or/integrity in muscle cells lacking functional dystrophin in a subject in need thereof, the subject suffers from a dystrophic muscle disorder, such as DMD. In other aspects, the dystrophic muscle disorder is rhabdomyolysis or age-related muscle loss. In further aspects, the dystrophic muscle disorder is a muscular dystrophy sharing common features of decreased lipin-1 expression through increased expression of lipin-1. In some aspects, administering a therapeutically effective amount of a composition suitable for increasing expression of a LPIN1 gene or a lipin-1 protein levels in a muscle cell of said subject may reduce muscle fiber degeneration. In some aspects, administering a therapeutically effective amount of a composition suitable for increasing expression of a LPIN1 gene or a lipin-1 protein levels in a muscle cell of said subject may increase muscle mass, muscle strength, and/or exercise endurance. In some aspects administering a therapeutically effective amount of a composition suitable for increasing expression of a LPIN1 gene or a lipin-1 protein levels in a muscle cell of said subject may decrease centrally nucleated muscle fibers.

EXAMPLES

The following examples illustrate features of the present disclosure but are not intended to limit the scope of the disclosure.

Figure 1B:
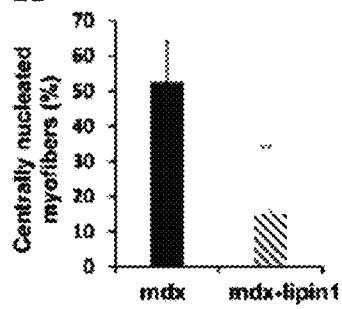
Figure 1C:
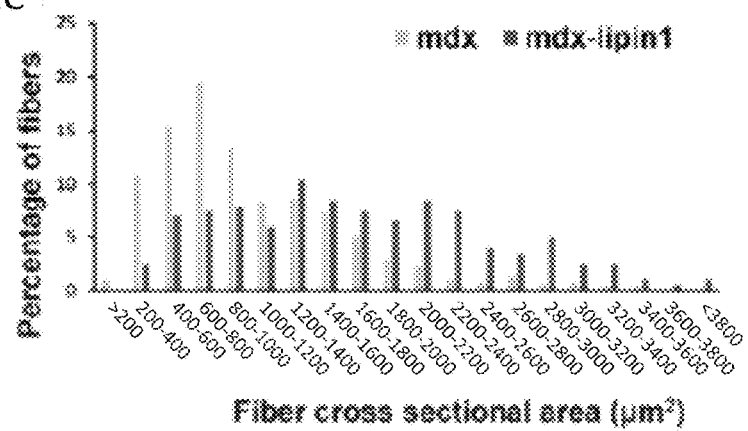

Restoration of Lipin-1 Levels Significantly Reduced Central Nucleation and Fiber Size Variability in Muscle Fibers of MDX Mice Experiments conducted during development of embodiments described herein demonstrate, for example, that restoration of lipin-1 protein levels significantly decreased centrally nucleated muscle fibers in mdx mice. To investigate the potential effects of lipin-1 restoration on the muscle phenotype, HA-tagged AAV1-lipin1 ($5×10^1$ viral genome particles (vg) per mouse) into the gastrocnemius of mdx mice at the age of 2 months via intramuscular injection. The gastrocnemius muscles were harvested for immunofluorescence at one-month after injection. Anti-HA antibody was used to determine lipin-1 restored regions; anti-laminin antibody was used to visualize individual myofibers and DAPI was used to detect nuclei. FIG. 1A shows a cryostat cross-section of harvested gastrocnemius muscles with immunofluorescent staining. Ten randomly selected cross-sections from each muscle were used. Arrows in the right panels of FIG. 1A indicate centrally nucleated myofibers characteristic of cumulative muscle regeneration. Mdx muscle fibers without lipin-1 restoration exhibited 52% centrally nucleated myofibers, which indicate that muscle fibers have undergone a cycle of degeneration and regeneration. FIG. 1B shows that in the lipin-1 restored regions, the percentage of centrally nucleated fibers was dramatically reduced to 13% compared with those in non-restored regions. FIG. 1C shows that myofiber sizes were noticeably larger when compared with those in non-restored regions as the mean myofiber cross-section area was increased from 1004 μm² in non-restored regions to 1725 μm² in lipin-1 restored regions.

Restoration of Lipin-1 Levels Inhibits Muscle Degeneration in MDX Mice

Figure 2A:
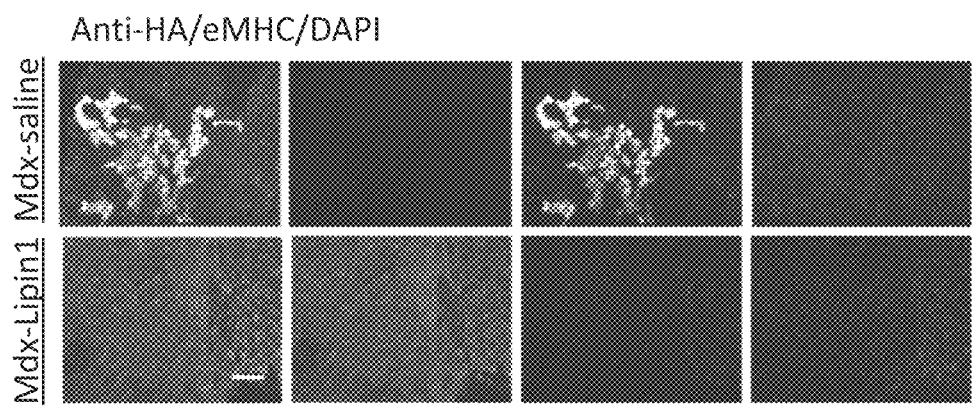
FIG. 2A-B demonstrates that restoring lipin-1 levels inhibits muscle degeneration in mdx mice.
Figure 2B:
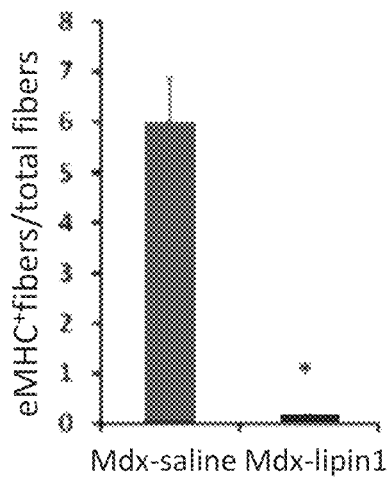

Experiments conducted during development of embodiments described herein demonstrate, for example, that restoration of lipin-1 protein levels inhibits muscle degeneration in mdx mice. Immunostaining with embryonic myosin heavy chain (eMHC) was used to assess the effects of lipin-1 restoration on current myofiber regeneration in dystrophic muscle. FIG. 2A-B shows that the proportion of eMHC-positive fibers was significantly less in AAV1-lipin1-treated mdc mice compared with those in saline-injected mdx mice one month after injection. These data indicate that lipin-1 restoration prevented muscle degeneration and reduced muscle regeneration in mdx mice.

Restoration of Lipin-1 Expression Improved Membrane Integrity in MDX Mice

Figure 3A:
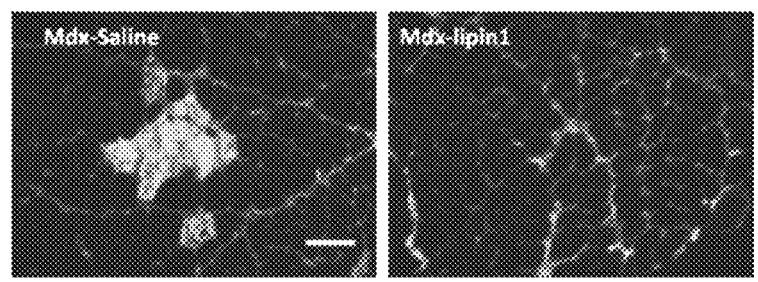
FIG. 3A-B demonstrates that restoring lipin-1 expression improved membrane integrity in mdx mice.
Figure 3B:
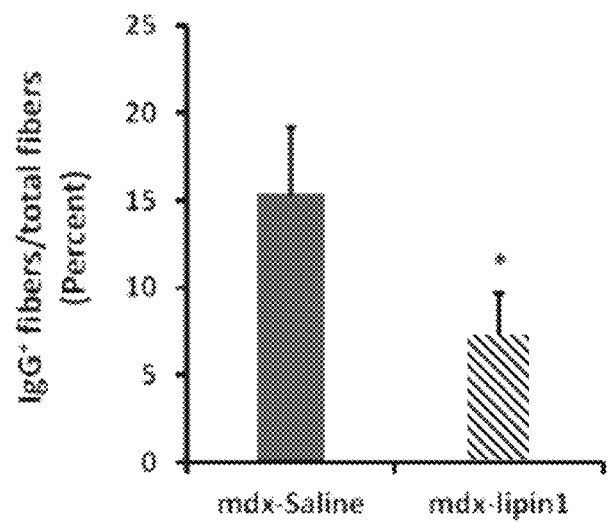

Experiments conducted during development of embodiments described herein demonstrate, for example, that restoration of lipin-1 levels improved membrane integrity in mdx mice. The loss of dystrophin in mdx mice results in membrane disruption and muscle damage during muscle contraction. In order to determine whether restoring lipin-1 protein levels might lead to an amelioration of muscle damage in mdx mice, gastrocnemius muscle sections from AAV1-lipin1-treated mdx mice and saline-injected mdx mice were stained with the muscle membrane impermeable market IgG, as illustrated in FIG. 3A. FIG. 3A-B shows that lipin-1 restored mdx mice showed markedly less intracellular fiber IgG staining than the saline-injected mice, suggesting lipin-1 protein restoration increased sarcolemma stability and reduced muscle damage in mdx mice.

Restoration of Lipin-1 Levels Increased Exercise Endurance and Contractile Force in MDX Mice Experiments conducted during development of embodiments described herein demonstrate, for example, that restoration of a lipin-1 levels significantly increased exercise endurance and contractile force in mdx mice. To evaluate the effect of restoration of lipin-1 expression on muscle performance, AAV1-lipin1 was intramuscularly injected in gastrocnemius muscle of 2-month-old male mdx mice. Mdx male littermates injected with saline and B10-WT mice were used as controls. One month after injection, the gastrocnemius were harvested for Western blotting to detect the levels of a lipin-1 protein expression in these groups of mdx mice. This Western blot and quantification of the Western blot bands are shown in FIG. 4A and FIG. 4B, respectively.

Figure 4A:
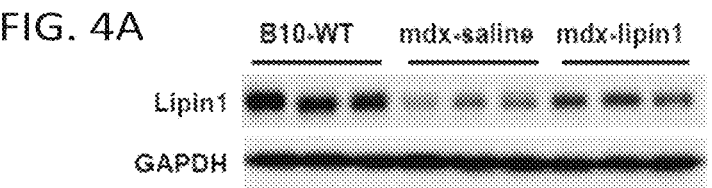
FIG. 4A-B demonstrates that restoring lipin-1 levels increased exercise endurance in mdx mice.
Figure 4B:
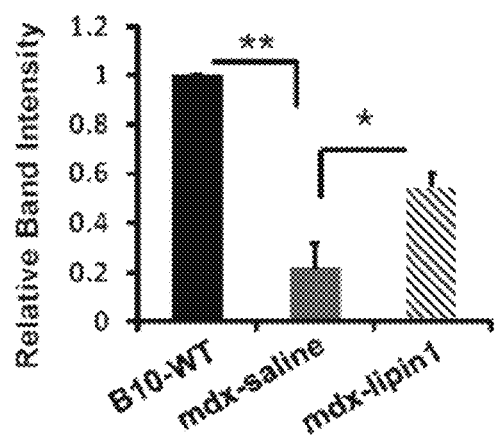
Figure 4C:
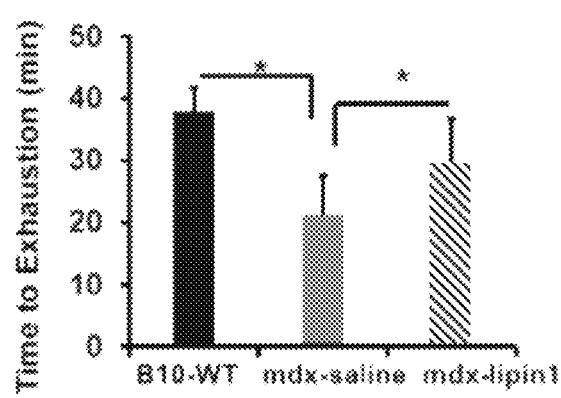
FIG. 4C demonstrates that restoring lipin-1 levels increased treadmill test time-to-fatigue in mdx mice. One month after their injection, B10-WT, mdx-saline, and mdx-lipin1 mice were placed on a treadmill to run with an upward inclination of 15°, at 5 meters per minute for 5 minutes, 10 meters per minute for 5 minutes, 15 meters per minute for 5 minutes, 20 meters per minute for 5 minutes, and 25 meters per minute until exhaustion. These mice were encouraged to run by using a mild electric shock grid at the end of the treadmill (0.2 mA, pulse 200 ms, 1 Hz). The experimental mice were considered to be exhausted after their refusal to remain on the treadmill belt for more than 5 seconds.

Time to exhaustion running on a treadmill was measured in same experimental setting as the Western blot shown in FIG. 4A and FIG. 4B, as shown in FIG. 4C. One month after their injection, B10-WT, mdx-saline and mdx-lipin1 mice were placed on a treadmill to run with an upward inclination of 15°, at 5 meters per minute for 5 minutes, 10 meters per minute for 5 minutes, 15 meters per minute for 5 minutes, 20 meters per minute for 5 minutes, and 25 meters per minute until exhaustion. These mice were encouraged to run by using a mild electric shock grid at the end of the treadmill (0.2 mA, pulse 200 ms, 1 Hz). The experimental mice were considered to be exhausted after their refusal to remain on the treadmill belt for more than 5 seconds. FIG. 4C shows that the mdx mice had reduced running endurance compared to B10-WT mice, and that restoring their lipin-1 levels increased treadmill test time-to-fatigue, compared to mdx mice.

Figure 5A:
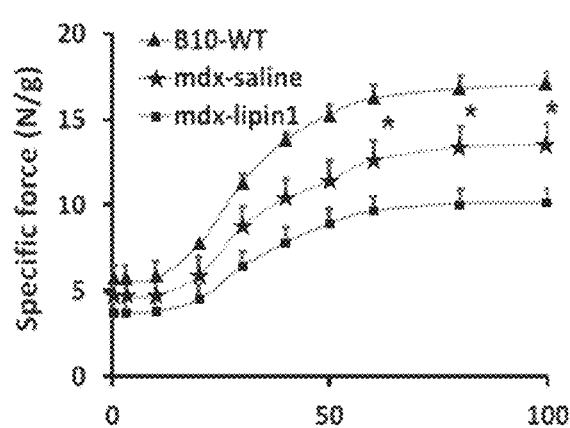
FIG. 5A-B demonstrates that restoring lipin-1 levels regained contractile force in mdx mice.
Figure 5B:
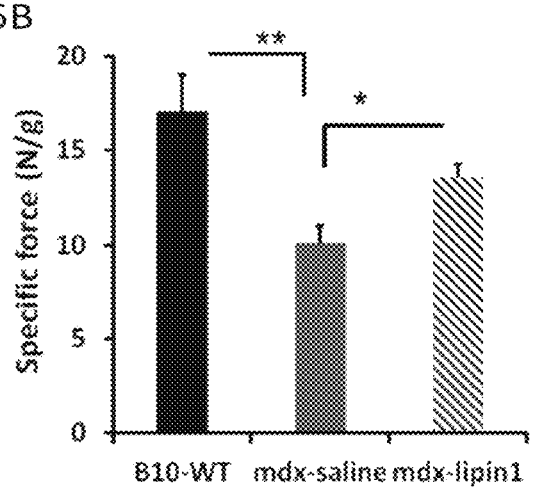

In order to further assess the physiological role of lipin-1 restoration, gastrocnemius muscles from B10-WT, mdx, and AAV1-lipin1-treated mdx mice were used to measure their contractile force in situ. As shown in FIG. 5A-B, mdx mice exhibited a ~44% reduction in gastrocnemius-specific force (force normalized to fiber weight) compared with controls. FIG. 5A illustrates significant force improvement in lipin-1 restored mdx mice compared to saline treated mice. FIG. 5B shows that AAV1-lipin1 treatment prevented the loss of maximal gastrocnemius force-generating capacity (mean rescue of ~50% relative to untreated mdx muscle at 100 Hz). These data indicate that lipin-1 restoration effectively alleviates the reduction in specific force of mdx mice.

Over-Expression of LPIN1 in Mice Provides a Protective Effect

Figure 6A:
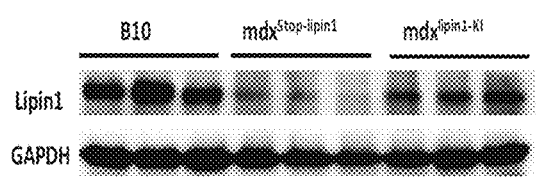
FIG. 6A-C demonstrates that transgenic lipin1 overexpression in mdx mice reduces membrane damage.
Figure 6B:
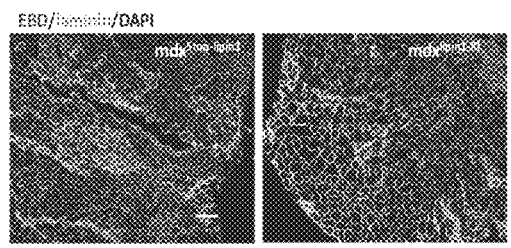
Figure 6C:
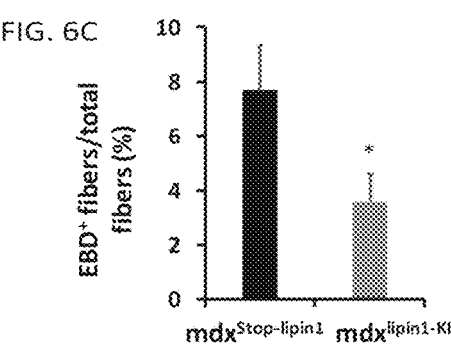
Figure 6D:
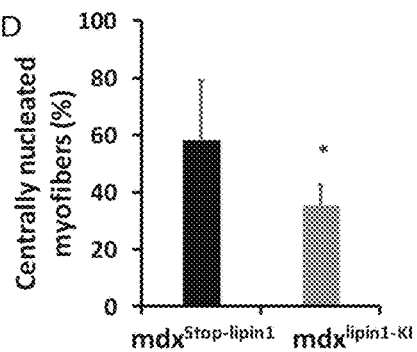

Transgenic mice provide a more uniform and sustained level of transgene expression compared to intramuscular delivery. To generate a reliable and reproducible approach to assessing the effect of lipin1 overexpression in mdx mice, mdx$^{lipin1-KI}$ transgenic mice were generated by crossing skeletal muscle-specific lipin1-overexpressing mice (Rosa26-Stop-lipin1) with mdx mice. To determine whether lipin1 overexpression in mdx muscle can protect plasma membrane from mechanical damage, Evans Blue dye (1 mg EBD/0.1 ml PBS/10 gBM) was injected into the gastrocnemius of mdx$^{lipin1-KI}$ transgenic mice and their control littermates (mdx$^{Stop-lipin1}$). As shown in FIG. 6, it was found that mdx$^{liPin1-KI}$ transgenic mice had significant reduced muscle membrane leakage of EBD compared to their control littermates. FIG. 6A-C demonstrates that transgenic lipin1 overexpression in mdx mice reduces membrane damage. FIG. 6A shows a Western blot of lipin1 expression in B10 WT, mdx$^{Stop-lipin1}$ controls and transgenic mdx$^{lipin1-KI}$ mice. FIG. 6B shows representative immunofluorescence images of EBD staining in gastrocnemius sections from these mice. Muscle sections were immunostained with laminin (green) and counter-stained with DAPI (blue) (scale bar=100 μm); FIG. 6C shows quantitation of EBD positive fibers; and, FIG. 6D shows centrally nucleated myofibers as a percentage of total fibers in composited images (*p<0.05; n=6 mice/group). This data confirms that lipin1 overexpression could ameliorate myofiber membrane damage in mdx mice.

Figure 7A:
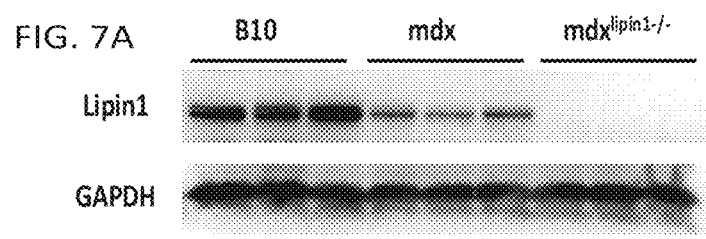
FIG. 7A-B demonstrates effects of further knockdown of lipin1 on muscle integrity in mdx mice.
Figure 7B:
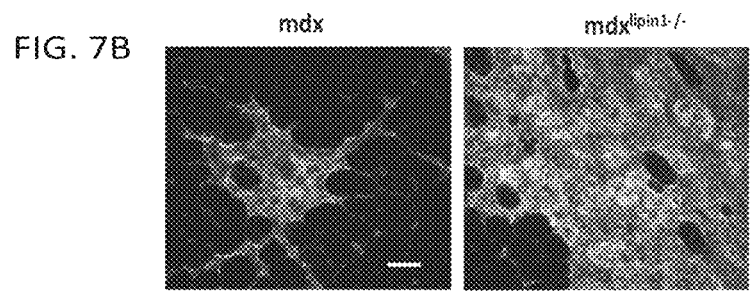

To determine whether lipin1 has protective role in maintaining membrane integrity independent of dystrophin lipin1 was knocked down in mdx mice (mdx$^{lipin1-/-}$) by crossing mdx mice with skeletal muscle specific lipin1 deficient mice. Gastrocnemius muscle was stained with the membrane impermeable marker IgG (FIG. 7). FIG. 7A-B demonstrates Effects of further knockdown of lipin1 on muscle integrity in mdx mice. FIG. 7A shows a Western blot of lipin1 expression in B10 WT, mdx controls and mdx$^{lipin1-/-}$ mice. FIG. 7B shows representative immunofluorescence images of IgG staining in gastrocnemius sections from mdx and mdx$^{lipin1-/-}$ mice. Scale bar=100 μm. It was found that mdx$^{lipin1-/-}$ mice had significantly increase IgG staining compared to mdx mice. These data suggest that further knockdown lipin1 induced much severe membrane damage and lipin1 has protective role in maintaining membrane integrity independent of dystrophin.

The data evidence that lipin1 overexpression can serve as a therapy to re-establish membrane stability, restore muscle function and improve survival. Discovering a therapeutic role for lipin1 upregulation can be expected to have a sustained and transformative impact on the treatment of DMD.

Stimulation of Lipin-1 Protein Expression by Rosiglitazone

Figure 8:
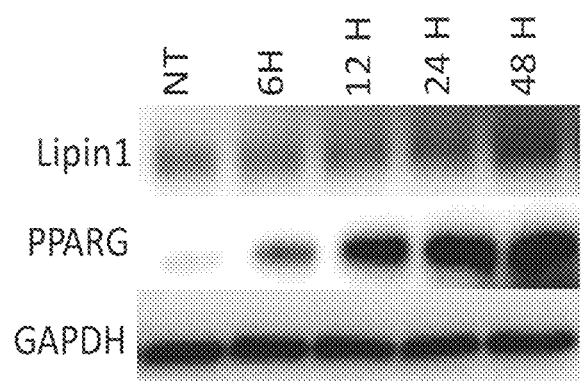
FIG. 8 demonstrates that rosiglitazone can be used as a drug to activate lipin1 expression. C2C12 myoblasts were treated with differentiation medium for 4 days after confluence. At day 4, differentiated myotubes were treated with 10 μM of rosiglitazone at 0, 6 h, 12 h, 24 h, and 48 h. Cell lysates were harvested after the treatment and protein expression levels of lipin1 and PPAR-gamma were assessed using western blot.

Lipin1 protein expression levels can be upregulated by rosiglitazone treatment in vitro (FIG. 8). FIG. 8 demonstrates that rosiglitazone can be used as a drug to activate lipin1 expression. C2C12 myoblasts were treated with differentiation medium for 4 days after confluence. At day 4, differentiated myotubes were treated with 10 μM of rosiglitazone at 0, 6 h, 12 h, 24 h, and 48 h. Cell lysates were harvested after the treatment and protein expression levels of lipin1 and PPAR-gamma were assessed using western blot. Since rosiglitazone is FDA approved drug for type 2 diabetes, and small size of these pharmaceuticals give them an advantage over gene therapy vectors. These data show that rosiglitazone treatment may serve as a therapeutic alternative to re-establish membrane stability through lipin1 upregulation and may have a sustained and transformative impact on the treatment of muscular dystrophy.

Any patents or patent publications or other literature mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

What is claimed is:

1. A method of treating muscle weakness and wasting in a subject in need thereof, wherein the subject has Duchenne's muscular dystrophy (DMD), the method comprising administering to a muscle cell of the subject a therapeutically effective amount of a composition suitable for causing expression of a lipin-1 protein in the muscle cell of said subject, wherein the composition comprises an expression vector comprising a nucleotide encoding a lipin-1 protein.

2. The method of claim 1, wherein the nucleotide is a LPIN1 gene.

3. The method of claim 1, wherein the nucleotide is operably placed in a vector.

4. The method of claim 3, wherein the vector is derived from a virus.

5. The method of claim 4, wherein the virus is selected from the group consisting of an adeno-associated virus ("AAV"), a retrovirus, a lentivirus, an adenovirus, a herpes simplex virus, a cytomegalovirus, a poxvirus, a Simian virus 40 (SV40) an Epstein-Barr virus or combinations thereof.

6. The method of claim 3, wherein the vector comprises a promoter to regulate expression of the lipin-1 protein.

7. The method of claim 6, wherein the promoter is selected from the group consisting of an α skeletal muscle actin promoter, a myosin light chain 3F promoter, or a muscle creatine kinase promoter.

8. The method of claim 6, wherein the vector further comprises a muscle-specific enhancer.

9. The method of claim 8, wherein the muscle-specific enhancer is an SV40 enhancer.

10. The method of claim 3, wherein the vector is a plasmid.

11. The method of claim 1, wherein said expression vector comprises a plasmid delivery system comprising said nucleotide encoding a lipin-1 protein.

12. The method of claim 11, wherein the plasmid delivery system further comprises one or more of a lipid, a liposome, a polymer, a lipoplex, a peptide, and a protein.

13. The method of claim 12, wherein the lipid in the plasmid delivery system is cationic.

14. The method of claim 12, wherein the polymer in the plasmid delivery system is non-ionic.

15. The method of claim 14 wherein the polymer comprises poly N-vinyl pyrrolidone.

16. The method of claim 12, wherein the peptide or protein comprises one or more of a poly-L-lysine, a viral fusion peptide, a transferrin, a GALA peptide, and a KALA peptide.

17. The method of claim 11, wherein the plasmid delivery system comprises a mix of block co-polymers and pluronics L61 and F127.

18. The method of claim 11, wherein the plasmid delivery system further comprises CRISPR and Cas-9.

19. The method of claim 1, further comprising co-administration of retinoic acid and/or trichostatin.

20. The method of claim 1, wherein the composition further comprises rosiglitazone.

21. The method of claim 1, wherein the composition further comprises an agent selected from the group consisting of a peroxisome proliferator-activated receptor y coactivator 1 a (PGC-la) agonist, a sterol regulatory element binding protein (SREBP) agonist, nuclear factor Y, dexamethasone, formoterol, a NOR-1 agonist or combinations thereof.

22. The method of claim 1, wherein expressing lipin-1 protein in the muscle increases muscle mass, muscle strength, and/or exercise endurance in the subject.

23. The method of claim 1, wherein the composition comprises said expression vector comprising a nucleotide encoding a lipin-1 protein and at least one of a PGC-la agonist, an SREBP agonist, a NOR-1 agonist, dexamethasone, or formoterol.

* * * * *